United States Patent
Pinkos et al.

(10) Patent No.: US 6,794,546 B2
(45) Date of Patent: Sep. 21, 2004

(54) CONTINUOUS PREPARATION OF ALKENYL COMPOUNDS

(75) Inventors: Rolf Pinkos, Bad Dürkheim (DE); Rudolf Erich Lorenz, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/309,178

(22) Filed: Dec. 4, 2002

(65) Prior Publication Data

US 2003/0105354 A1 Jun. 5, 2003

(30) Foreign Application Priority Data

Dec. 5, 2001 (DE) .......................................... 101 59 673

(51) Int. Cl.[7] ........................ C07C 41/01; C07D 233/54
(52) U.S. Cl. ..................................... 568/579; 548/335.1
(58) Field of Search ........................ 568/579; 548/335.1

(56) References Cited

U.S. PATENT DOCUMENTS

| | | | |
|---|---|---|---|
| 5,665,889 A | 9/1997 | Chu et al. | |
| 5,726,321 A | 3/1998 | Bittins et al. | 548/335 |
| 6,384,216 B1 * | 5/2002 | Lorenz et al. | 540/540 |

FOREIGN PATENT DOCUMENTS

| | | | |
|---|---|---|---|
| DE | 1 163 835 | | 2/1964 |
| DE | 32 15 093 | | 1/1983 |
| DE | 100 02469 | | 7/2001 |
| JP | 10-182536 | * | 7/1998 |
| WO | 01/46139 | | 6/1991 |
| WO | 01/46141 | | 6/2001 |

OTHER PUBLICATIONS

Ullmann's Enc. of Ind. Chem, 6th Ed.Vinyl Ethers, 1–6 and 1–2.
Justus Liebigs, Am. Chem.601(1956)Reppe et al, 135–138.

* cited by examiner

Primary Examiner—Shailendra Kumar
(74) Attorney, Agent, or Firm—Keil & Weinkauf

(57) ABSTRACT

A continuous process for the preparation of O—, S— and N-alkenyl compounds by reaction of the corresponding OH, SH or NH compound with an acetylene in the liquid phase in the presence of basic alkali or alkaline earth metal compounds at from 40 to 300° C. and from 0.11 to 5 MPa absolute comprises continuously feeding the corresponding OH, SH or NH compound and the acetylene and operating at a conversion of the corresponding OH, SH or NH compound of $\geq 90\%$.

9 Claims, No Drawings

CONTINUOUS PREPARATION OF ALKENYL COMPOUNDS

The present invention relates to a continuous process for the preparation of O—, S— and N-alkenyl compounds by reaction of the corresponding OH, SH or NH compound with an acetylene in the liquid phase in the presence of basic alkali or alkaline earth metal compounds at from 40 to 300° C. and from 0.11 to 5 MPa absolute.

Alkenyl compounds represent an important class of compound with a wide range of applications. Alkenyl ethers, for instance, find use as monomeric building blocks in polymers and copolymers, in coatings, adhesives, printing inks and also in radiation-curable coatings. Further areas of application are the production of intermediates, scent and aroma chemicals, and also pharmaceutical products. Alkenylamides are used as monomers in the production of plastics and coatings. Polyvinylamides are used, for example, as laundry detergent ingredients, as adjuvants in cosmetic and medicinal products and also to stabilize and clarify beers and fruit juices. Polyvinyllactams, in particular polyvinylpyrrolidone polymers, have a wide range of uses and serve, for example, as dispersants for pigments, as laundry detergent ingredients, as adjuvants in cosmetic and medicinal products and also as assistants in textile processing and adhesive technology.

The industrial production of vinyl compounds is carried out in general by reaction of the corresponding active-hydrogen compounds, such as alcohols, amides or amines, with ethyne in the presence of basic catalysts (see Ullmann's Encyclopedia of Industrial Chemistry, $6^{th}$ edition, 2000 Electronic Release, Chapter "VINYL ETHERS—Production" and W. Reppe et al., Justus Liebigs Ann. Chem., 601 (1956), pages 135 to 138). The vinylation can take place in both the liquid phase and the gas phase. Vinylation in the gas phase employs basic heterogeneous catalysts, such as KOH on activated carbon or MgO or CaO. In the liquid phase, the strongly exothermic reaction is generally carried out in the presence of alkali metal hydroxide or alkali metal alkoxide catalysts.

DE-B 1 163 835 describes the batchwise preparation of N-vinyl lactams by vinylation of the corresponding lactam with ethyne in the presence of a basic sodium or potassium catalyst by dissolving ethyne in the liquid lactam and then heating the solution at a pressure of from 70 to 350 kg/cm² (6.9 to 34.3 MPa) to the reaction temperature of from 150 to 280° C. The adduced examples report conversions of from 36 to 55% and N-vinyl lactam selectivities ("yield based on reacted lactam") of from 78 to 95%.

DE-A 3 215 093 discloses a process for the vinylation of 2-pyrrolidone with ethyne in the presence of a basic alkali metal salt catalyst and of a polyoxyalkylene cocatalyst. Suitable polyoxyalkylene compounds are said to be crown ethers (for example 18-crown-6), polyoxyethylene, polyoxypropylene, optionally terminated by alkyl or phenyl groups. In a first step, the basic alkali metal salt catalyst is produced by heating potassium hydroxide with 2-pyrrolidone and the cocatalyst with removal of the water formed in the reaction. The subsequent vinylation is carried out batchwise in an autoclave. Conversions of up to 63% and selectivities of 90% were obtained, which corresponds to a maximum yield of 57%.

U.S. Pat. No. 5,665,889 describes a process for the preparation of N-vinyl-2-pyrrolidone from 2-pyrrolidone and ethyne in the presence of basic alkali metal compounds that uses ether oligomers with hydroxy end groups, such as polytetrahydrofuran, or linear diols with at least 4 carbon atoms, such as 1,4-butanediol, as cocatalysts. The vinylation is carried out at a temperature of 100 to 200° C., a pressure of 7.5 to 30 atm (0.76 to 3 MPa) and a reaction time of several hours. In a first step, the basic alkali metal salt catalyst is produced by heating potassium hydroxide with 2-pyrrolidone and the cocatalyst with removal of the water formed in the reaction. The subsequent vinylation is carried out batchwise in an autoclave. The use of 1,4-butanediol results, even after a reaction time of 4 hours, in a yield of only 77.2%.

DE-A 100 02 469 teaches a process for the alkenylation of tertiary alcohols in the presence of a basic alkali metal compound, wherein the tertiary alcohols are converted to a maximum of 90%, the crude product obtained is extracted with water and the tertiary alkenyl alkyl ethers are recovered from the organic phase. Conduction of the reaction by batchwise, semicontinuous or continuous means is described.

WO 01/46141, WO 01/46139 and DE-A 100 17 222 teach processes for the preparation of N-alkenylamides and alkenyl ethers in the presence of basic alkali metal compounds and a 1,2-diol, a 1,3-diol or a mono- or diether of 1,4-butanediol as cocatalyst. The alkenylation is carried out at a temperature of from 100 to 200° C., an ethyne partial pressure of smaller than 5 MPa and a reaction time of several hours. In a first step, the basic alkali metal catalyst is produced by heating potassium hydroxide with NH-amide or with alcohol and the cocatalyst with removal of the water formed in the reaction. The subsequent vinylation is carried out batchwise in an autoclave. After a reaction time of 12 hours, conversions of up to 96.3% and yields of N-vinylamides of up to 90.5% were obtained from the vinylation of NH-amides and conversions of up to 97.7% and yields of vinyl ethers of up to 90.9% were obtained from the vinylation of alcohols. A variant is also described in which the NH-amide or the alcohol and the ethyne are fed to a continuous loop reactor, where a corresponding amount of the reaction solution is continuously removed.

The customary industrial semicontinuous processes, in which the component to be alkenylated is initially charged together with the basic catalyst and the alkyne is continuously added until the end of the reaction, have the disadvantages of the time-, work- and energy-intensive process steps of filling, heating, pressurizing, cooling, depressurizing and emptying of the reaction apparatus, in particular during the preparation of quantities which require several reaction batches. Furthermore, a greater range of relative concentrations of the reactants and products is present during semicontinuous synthesis, which can lead to a conversion-dependent reaction rate and promotes the formation of undesirable byproducts. These disadvantages result in a lower selectivity and, taking into account the necessary preparation times, also a much lower space-time yield than would be expected on the basis of the chemical reaction rate.

It is an object of the present invention to provide a process for the preparation of O—, S— and N-alkenyl compounds by reaction of the corresponding O, S or N compound with an acetylene, that does not have the above disadvantages, allows the preparation of O—, S— and N-alkenyl compounds with high selectivity, high space-time yield and high productivity in a simple way and only forms small amounts of substantially involatile residues.

We have found that this object is achieved by a continuous process for the preparation of O—, S— and N-alkenyl compounds by reaction of the corresponding OH, SH or NH compound with an acetylene in the liquid phase in the presence of basic alkali or alkaline earth metal compounds at from 40 to 300° C. and from 0.11 to 5 MPa absolute, which comprises continuously feeding the corresponding OH, SH or NH compound and the acetylene and operating at a conversion of the corresponding OH, SH or NH compound of ≧90%.

An essential of the process of the invention is that it is conducted at a conversion of the corresponding OH, SH or NH compound of ≧90%, preferably of ≧92%, particularly preferably of ≧95% and very particularly preferably of ≧97%. The desired conversion at the desired temperature and pressure is achieved by the continuous feeding of OH, SH or NH compound and the acetylene at corresponding rates. The term "continuous feeding" also comprehends fluctuations in the amount added, up to an intermittent addition, as long as the specified ratio of amounts in the reactor is achieved.

The conversion C of the corresponding OH, SH or NH compound is calculated from the amount of the continuously fed OH, SH or NH compound per unit time $\dot{n}_{in}$ and the amount of the continuously removed OH, SH or NH compound per unit time $\dot{n}_{out}$ according to the formula $$C = 1 - \frac{\dot{n}_{out}}{\dot{n}_{in}}$$

In general, the conversion obtained is analytically monitored, either continuously or periodically or at irregular intervals. The precise adjustment of the rates mentioned can be carried out, for example, manually or completely automatically by direct analysis of analytical results by a closed-loop control system. It is sensible to work with a small excess of acetylene, which, for example, can be achieved by producing an off-gas stream containing acetylene. The acetylene content can, for example, be ascertained by IR measurement.

The process of the invention is surprising in that unexpectedly the reaction rate increases significantly at a conversion of ≧90% and therefore a significantly higher space-time yield is achievable than at conversions of smaller than 90%. Moreover, conversions ≧90% are generally associated with the formation in the reaction system of an insoluble phase which contains the basic alkali or alkaline earth metal compound and the fraction of which increases with rising conversion.

Useful OH, SH or NH compounds for the process of the invention include alcohols and phenols (—OH), thiols and thiophenols (—SH), NH-amides (—CO—NH—) and NH-amines (—NH—).

Useful alcohols for the process of the invention include all unbranched and branched, acyclic and cyclic, saturated and unsaturated, aliphatic and aromatic alcohols having from 1 to 22 carbon atoms and at least one hydroxyl group attached to a nonaromatic carbon, and their derivatives.

Useful acyclic aliphatic alcohols include, for example, methanol, ethanol, 1-propanol, 2-propanol, 1-butanol, 2-butanol (sec. butanol), 2-methyl-1-propanol (isobutanol), 1-methyl-2-propanol (tert. butanol), 1-pentanol, 2-pentanol, 3-pentanol, 2-methyl-1-butanol, 3-methyl-1-butanol (isoamyl alcohol), 2,2-dimethyl-1-propanol, 2-methyl-2-butanol, 3-methyl-2-butanol, 1-hexanol, 2-hexanol, 3-hexanol, 3,3-dimethyl-3-butanol, 4-methyl-2-pentanol, 2-ethyl-1-butanol, cis-3-hexen-1-ol, 5-hexen-1-ol, 1-heptanol, 2-heptanol, 3-heptanol, 2,4-dimethyl-3-pentanol, 1-octanol, 2-octanol, 3-octanol, 2-ethyl-1-hexanol, 2,4,4-trimethyl-1-pentanol, 1-nonanol, 2-nonanol, 3-nonanol, 4-nonanol, 5-nonanol, 1-decanol, 2,2-dimethyl-1-octanol, 1-dodecanol, 1-tetradecanol (myristyl alcohol), 1-hexadecanol (cetyl alcohol), 1-octadecanol (stearyl alcohol), cis-9-octadecen-1-ol (oleyl alcohol), cis,cis-9,12-octadecadien-1-ol, cis,cis,cis-9,12,15-octadecatrien-1-ol, 1-eicosanol (arachyl alcohol) and 1-docosanol (behenyl alcohol).

Useful cyclic aliphatic alcohols include, for example, cyclopropanol, cyclopropylmethanol, cyclopropylethanol, cyclobutanol, cyclobutylmethanol, cyclobutylethanol, cyclopentanol, cyclopentylmethanol, cyclopentylethanol, 1-methylcyclopentanol, 2-methylcyclopentanol, 3-methylcyclopentanol, cyclohexanol, cyclohexylmethanol, cyclohexylethanol, 1-methylcyclohexanol, 2-methylcyclohexanol, 3-methylcyclohexanol, 4-methylcyclohexanol, cycloheptanol, cyclooctanol and cyclodecanol.

Useful aromatic alcohols include, for example, benzyl alcohol, hydroxydiphenylmethane, 1-phenylethanol, 2-phenylethanol, 2,2-diphenylethanol, 2,2,2-triphenylethanol, 1-naphthyl alcohol and 2-naphthyl alcohol.

Useful polyhydric alcohols include, for example, 1,2-ethanediol, 1,2-propanediol, 1,3-propanediol, 1,2-butanediol, 1,4-butanediol, 1,5-pentanediol, 1,6-hexanediol, diethylene glycol, triethylene glycol, tetraethylene glycol, 1,2,3-propanetriol (glycerol) and 2-methyl-1,2,3-propanetriol.

Useful phenols for the process of the invention include all compounds having from 1 to 12 carbon atoms that have at least one hydroxyl group attached to an aromatic carbon, and derivatives thereof.

Useful phenols include, for example, phenol, 2-methylphenol (o-cresol), 3-methylphenol (m-cresol), 4-methylphenol (p-cresol), 2-ethylphenol (o-cresol), 3-ethylphenol (m-cresol), 4-ethylphenol (p-cresol), 2,3-dimethylphenol, 2,4-dimethylphenol, 2,5-dimethylphenol, 2,6-dimethylphenol, 3,4-dimethylphenol, 3,5-dimethylphenol, 1-naphthol and 2-naphthol.

Compounds can also be used that contain both alcoholic and phenolic hydroxyl groups, such as, for example, 2-(4'-hydroxyphenyl)ethanol.

Alcohols preferably used in the process of the invention are aliphatic, acyclic and cyclic alcohols. Methanol, ethanol, propanol, 2-propanol, 1-butanol, 2-methyl-1-propanol (isobutanol), cyclopentanol, cyclohexanol, 1,2-ethanediol, diethylene glycol, triethylene glycol, 1,3-propanediol, 1,4-butanediol and 1,6-hexanediol are particularly preferred.

Useful thiols for the process of the invention include all unbranched and branched, acyclic and cyclic, saturated and unsaturated, aliphatic and aromatic thiols having from 1 to 22 carbon atoms and at least one thiol group attached to a nonaromatic carbon, and their derivatives.

Useful acyclic aliphatic thiols include, for example, methanethiol, ethanethiol, 1-propanethiol, 2-propanethiol, 1-butanethiol, 2-butanethiol (sec. butanethiol), 2-methyl-1-propanethiol, 1-pentanethiol and 1-hexanethiol. Useful cyclic aliphatic thiols include, for example, cyclopentanethiol and cyclohexanethiol. Useful polyfunctional thiols include, for example, 1,2-ethanedithiol, 1,3-propanedithiol and 1,4-butanedithiol.

Useful thiophenols for the process of the invention include all compounds having from 1 to 12 carbon atoms that contain at least one thiol group attached to an aromatic carbon, such as thiophenol, and derivatives thereof.

Useful NH-amides for the process of the invention include all unbranched and branched, acyclic and cyclic, saturated and unsaturated, aliphatic and aromatic, secondary NH-amides having from 1 to 22 carbon atoms and their derivatives.

Useful acyclic amides include, for example, the NH-alkylamides of the branched and unbranched, saturated and unsaturated $C_1$- to $C_{22}$-carboxylic acids, with branched and unbranched, saturated and unsaturated, $C_1$- to $C_{10}$-alkyl groups on the amide nitrogen. Examples of acyclic NH-amides are the methyl-, ethyl-, propyl-, 1-methylethyl-, butyl-, 1-methylpropyl-, 1,1-dimethylethyl-, pentyl-, hexyl, heptyl-, octyl-, nonyl- or decylamides of formic acid, acetic acid, propionic acid, butyric acid, valeric acid, isovaleric acid, pivalic acid, caproic acid, 2-ethylbutyric acid, heptanoic acid, octanoic acid, 2-ethylhexanoic acid, nonanoic acid, isononanoic acid, decanoic acid, neodecanoic acid, lauric acid, myristic acid, palmitic acid, stearic acid, oleic acid, linoleic acid, linolenic acid, arachidinic acid and docosanoic acid. From the range of the acyclic NH-amides, N-methylacetamide, N-methylpropionamide and N-ethylacetamide are preferably used.

Preferred NH-amides are the cyclic NH-amides, which are known as NH-lactams. NH-lactams preferably used in the process of the invention are the 4- to 12-membered NH-lactams, such as 2-pyrrolidone, 2-piperidone, ε-caprolactam and their alkyl derivatives, such as 3-methyl-2-pyrrolidone, 4-methyl-2-pyrrolidone, 5-methyl-2-pyrrolidone, 3-ethyl-2-pyrrolidone, 3-propyl-2-pyrrolidone, 3-butyl-2-pyrrolidone, 3,3-dimethyl-2-pyrrolidone, 3,5-dimethyl-2-pyrrolidone, 5,5-dimethyl-2-pyrrolidone, 3,3,5-trimethyl-2-pyrrolidone, 5-methyl-5-ethyl-2-pyrrolidone, 3,4,5-trimethyl-2-pyrrolidone, 3-methyl-2-piperidone, 4-methyl-2-piperidone, 5-methyl-2-piperidone, 6-methyl-2-piperidone, 6-ethyl-2-piperidone, 3,5-dimethyl-2-piperidone, 4,4-dimethyl-2-piperidone, 3-methyl-ε-caprolactam, 4-methyl-ε-caprolactam, 5-methyl-ε-caprolactam, 6-methyl-ε-caprolactam, 7-methyl-ε-caprolactam, 3-ethyl-ε-caprolactam, 3-propyl-ε-caprolactam, 3-butyl-ε-caprolactam, 3,3-dimethyl-ε-caprolactam or 7,7-dimethyl-ε-caprolactam.

Particularly preferred NH-amides in the process of the invention are the unsubstituted 4- to 12-membered NH-lactams

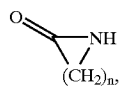

where n is in the range from 2 to 10, such as β-propiolactam, 2-pyrrolidone (γ-butyrolactam), 2-piperidone (δ-valerolactam), ε-caprolactam and also their alkyl-substituted derivatives. Very particularly preferred is the use of 2-pyrrolidone (γ-butyrolactam), 2-piperidone (δ-valerolactam) and ε-caprolactam.

Useful NH-amines for the process of the invention include all unbranched and branched, acyclic and cyclic, saturated and unsaturated, aliphatic and aromatic, secondary NH-amines having from 1 to 22 carbon atoms and their derivatives.

Useful acyclic amines include, for example, the di-$C_1$- to $C_{22}$-alkylamines with branched and/or unbranched alkyl radicals, such as dimethylamine, diethylamine, di-(1-propyl)amine, di-(2-propyl)amine, di-(1-butyl)amine, di-(2-butyl)amine, di-(2-methyl-1-propyl)amine, dipentylamine, dihexylamine, diheptylamine, dioctylamine, dinonylamine and didecylamine.

Useful cyclic amines include, for example, the 4- to 12-membered cyclic amines, such as azetidine, pyrrolidine, pyrrole, piperidine, imidazole, benzimidazole and morpholine.

Preferred amines include imidazole, 2-methylimidazole, 4-methylimidazole and 5-methylimidazole.

Preferred acetylenes for the process of the invention include unbranched and branched alkynes having from 2 to 6 carbon atoms and a terminal triple bond. The use of ethyne, propyne, 1-butyne, 1-pentyne and 1-hexyne is preferred, that of ethyne and propyne is particularly preferred, and that of ethyne is very particularly preferred.

The process of the invention generally involves the use of the basic alkali or alkaline earth metal compounds in an amount of from 0.05 to 15% by weight, preferably from 0.1 to 10% by weight and particularly preferably from 0.2 to 6% by weight, based on the reaction mixture.

Basic alkali and alkaline earth metal compounds that are generally used in the process of the invention are the oxides, hydroxides, alkanoates, thioalkanoates, phenolates, thiophenolates, and amides of lithium, sodium, potassium, cesium, magnesium and calcium. The alkali metal compounds are preferred, in particular the sodium and potassium compounds.

In a preferred embodiment, the alkali or alkaline earth metal $O^-$, $S^-$ or $N^-$ compounds and particularly preferably the sodium or potassium $O^-$, $S^-$ or $N^-$ compounds are used that correspond to the OH, SH or NH compounds to be used. They are obtainable, for example, by reacting the alkali or alkaline earth metals, the oxides, hydroxides or alkanoates thereof with the corresponding OH, SH or NH compound with removal of byproducts formed, which are hydrogen, water or alcohols. When oxides, hydroxides or alkanoates are used, these are generally heated together with the corresponding OH, SH or NH compound with vaporization of the water or volatile alcohol formed. Particularly preferred starting compounds for said reaction are sodium and potassium hydroxide and also the sodium or potassium $C_1$- to $C_4$-alkoxides, i.e., methoxide, ethoxide, 1-propoxide, 2-propoxide, 1-butoxide, 2-butoxide, 2-methyl-1-propoxide and 2-methyl-2-propoxide. Mixtures of different alkali and alkaline earth metal compounds are also possible.

The acetylene and the OH, SH or NH compound to be used are generally fed at their rate of consumption. The quantities introduced therefore correspond approximately to the stoichiometrically necessary quantities, corrected by possible influences such as discharge of unconverted reactants or byproduct formation. A small molar excess based on the introduced OH, SH or NH compound is preferred. The excess is usually in the range from 0.001 to 10 mol %, preferably 0.01 to 5 mol % and particularly preferably from 0.015 to 3 mol %.

In the process of the invention, it is possible and possibly advantageous to use cocatalysts. In certain cases, they can cause a reduction in the formation of byproducts. The use of cocatalysts is generally known and, for example, is described in DE-A 3 215 093, U.S. Pat. No. 5,665,889, DE-A 100 17 222, WO 01/46139 and WO 01/46141, which are explicitly incorporated herein by reference. Preferred examples of possible cocatalysts are polyoxyalkylene compounds (e.g., polyoxyethylene or polyoxypropylene) or divinyl compounds of diols (e.g., 1,2-divinyloxyethane or 1,4-divinyloxybutane). They are generally used in a quantity of from 2 to 30% by weight. Depending on the type and quantity of the cocatalyst used this can also be used as solvent. Preferred cocatalysts do not chemically react with the reaction components.

In the process of the invention, it is also possible and possibly advantageous to use solvents. Suitable solvents are relatively good solvents for both the OH, SH or NH compound and the basic alkali or alkaline earth metal compound to be used, chemically inert with regard to the compounds to be used, i.e., in particular they may not contain any acidic sites, which would react with the basic groups, and easy to separate from the system, preferably distillatively, after the synthesis of the O—, S— and N-alkenyl compound. Examples of preferred dipolar aprotic solvents are N-methylpyrrolidone, tetrahydrofuran and dialkyl ethers of glycols, di-, oligo- or polyglycols.

Furthermore, inert gases, for example nitrogen or noble gases, can be present during the operation of the process of the invention.

The alkenylation is generally carried out at a temperature in the range from 40 to 300° C., preferably from 60 to 230° C. and particularly preferably from 70 to 200° C. It is generally carried out at a pressure in the range from 0.11 to 5 MPa absolute, preferably from 0.15 to 3 MPa absolute and particularly preferably from 0.2 to 2 MPa absolute. The total pressure of the system is generally made up of the partial pressures of the components present in the reaction system. Possible components include for example any optionally added solvents or inert gases. Where low molecular weight acetylenes are used, such as ethyne, propyne or 1-butyne, an acetylene partial pressure of greater than 0.1 MPa is generally set. If higher acetylenes are used, their volatility can result in the acetylene partial pressure being very low and, for example, being well below 0.1 MPa. If ethyne is used as the acetylene, its partial pressure in the process of the invention is in general in the range from 0.11 to 5 MPa, preferably from 0.15 to 3 MPa, and particularly preferably from 0.2 to 2 MPa.

The process of the invention is preferably used for the preparation of alkenyl ethers, N-alkenylamides and N-alkenylamines and particularly preferably for the preparation of vinyl ethers, N-vinylamides and N-vinylamines. Particularly preferred products include vinyl 2-methyl-2-propyl ether (vinyl tert-butyl ether), vinyl 3-methyl-1-butyl ether (vinyl isoamyl ether), vinyl cyclohexyl ether, N-vinyl-2-pyrrolidone, N-vinyl-2-piperidone, N-vinyl-$\epsilon$-caprolactam, N-vinylpyrrolidine, N-vinylpyrrole, N-vinylpiperidine and N-vinylimidazole.

Useful reactors for the alkenylation in the process of the invention include in principle any apparatus described in the technical literature for gas-liquid reactions, or in the case of the use of liquid acetylenes, the known apparatus for liquid-liquid reactions. To obtain a high space-time yield an efficient introduction of the acetylene into the liquid phase and intensive mixing of the reaction mixture are important. The reaction of the process of the invention can be carried out in a single reactor or in plural successive reactors, for example a reactor battery. Suitable reactors include stirred-tank reactors, batteries of stirred tanks, flow tubes (preferably with internals), bubble columns and loop reactors. To ensure its efficient introduction, the acetylene is preferably introduced through the stirrer (in the case of a stirred tank or a stirred tank battery) and/or through nozzles.

In order to alkenylate unconverted OH, SH or NH compounds, it is preferable to use a supplementary reactor, for example a flow tube or a delay time tank downstream from the actual reactor (main reactor). In general, this supplementary reactor has a smaller volume than the main reactor and is usually operated without further addition of acetylene. To complete the reaction in the supplementary reactor, a delay time of from 0.1 to 0.5 hours is generally necessary. This allows conversions of up to 100%.

In order to minimize the risk of spontaneous reaction while working with gaseous acetylenes, in particular while working with ethyne, the process of the invention is preferably conducted in the absence of a continuous gas phase in the reaction apparatus. The phrase "continuous gas phase" refers to gas spaces within the reaction chamber whose size exceeds that of individual, discrete bubbles.

A continuous gas phase in the reaction apparatus can, for example, be avoided by continuous removal of the reaction mixture at the highest point of the reaction apparatus. Any gas bubbles arriving at the head of the reactor are generally flushed out of the reaction system straight away by the liquid stream. After leaving the reactor, the operating parameters, for example in a downstream phase separator, are selected such that this region is under safe conditions. This can be achieved, for example, by reduction of the pressure and/or temperature and/or by inertizing the mixture through addition of an inert gas.

As is described in EP-A 0 733 401, further measures can be taken in order to avoid a continuous gas phase in the reaction apparatus, alone or in combination:

a) One of the supplementary measures is the targeted controlling of the concentration of acetylene in the reactor effluent to a value below the maximum gas solubility, preferably 10 to 95%, particularly preferably 20 to 80% and very particularly preferably 30 to 80% of the maximum gas solubility. This prevents even the formation of free gas bubbles in the consequently unsaturated liquid, so that the head of the reactor is in general free of bubbles. The concentration of the acetylene in the reactor effluent is determined preferably as described in EP-A 0 733 401.

b) The other supplementary measure is the use of a jet nozzle, through which the reaction mixture removed by a circulation pump, preferably together with the fresh OH, SH or NH compound to be added, is injected. The impulse that is introduced into the reactor in this way induces an intensive circulation, which results in the redispersion of the gases present. In this way, the formation of larger bubbles as a precursor for a continuous gas phase is prevented.

The jet nozzle can be mounted at the base or the head of the reactor, where in the latter case a concentric internal tube parallel to the direction of flow of the introduced liquid flow is preferably located in the middle of the reactor. The placing of the jet nozzle at the highest point of the reactor has the advantage that when there is no circulation of liquid, no liquid can climb back into the gas-transporting part of the jet nozzle. The use of a self-aspirating jet nozzle represents an additional, integrated safety feature, since the failure of the circulation pump and therefore the liquid driving jet can result in no more gas being aspirated.

For the process of the invention, the jet nozzle systems described under b) are particularly preferred. The conduction of the reaction in a jet loop reactor is very particularly preferred. A jet loop reactor generally includes a jet nozzle located at the head of the reactor, a concentric internal tube and an impact plate. The corresponding OH, SH or NH compound, the acetylene and the reaction mixture removed by a circulation pump are introduced to the jet loop reactor by the jet nozzle and an intensive circulation is induced by the introduced impulse. A corresponding quantity of reaction mixture is continuously removed at the base of the reactor and is fed back to the jet nozzle via an external circulation pump and a heat exchanger (cooler). The reaction effluent is generally continuously removed from said circulation or at a separate point at the head of the reactor, preferably at the head of the reactor, and worked up by known methods. A distillation to give plural fractions is referred, with the required O—, S—, or N-alkenyl compound being separated off. The catalyst-containing phase that is obtained during the separation is preferably returned to the reactor. It is preferably likewise added through the jet nozzle.

In general the reaction mixture obtained is worked up and the O—, S—, or N-alkenyl compound in it is separated off. The separation is generally carried out distillatively, although, depending on needs and requirements, other separation procedures, such as crystallization, can also be used. The residue obtained after the separation, which contains the basic alkali or alkaline earth metal compound, can, depending on need, be disposed of, further worked up or returned to the reactor. A criterion here may be the cost/benefit ratio, for which availability and the value of the basic alkali or alkaline earth metal compound as well as of any unconverted OH, SH or NH compound can be pivotal. A continuous process is preferred in which a) an amount of a reaction mixture is continuously removed from the reactor that corresponds to the amounts that are continuously fed to the reactor;
b) the O—, S— or N-alkenyl compound is separated from the reaction mixture removed from the reactor; and
c) the mixture that contains the basic alkali or alkaline earth metal compound is returned to the reactor.

Depending on the quantity of the byproducts formed and their ease of separation from the catalyst-containing phase, a portion of the catalyst-containing phase is flushed out of the system to prevent an accumulation of undesired components.

In a preferred embodiment, a solution of potassium hydroxide and the corresponding OH, SH or NH compound is prepared and heated in a mixing vessel. The water of reaction formed is vaporized and removed at the head of the vessel. The solution then comprises the corresponding potassium O—, S— or N—compound as basic compound. The solution obtained, together with further OH, SH or NH compound, is then introduced into a jet loop reactor until it has been filled to the required level. The circulation pump is then switched on, the system is heated to the required temperature and the addition of ethyne is commenced, with the system being kept at the required pressure. Once a ratio of the quantity of the O—, S— or N-alkenyl compound to the sum of the quantities of the O, S or N compound and the O—, S— or N-alkenyl compound of $\geq 0.9$ has been achieved, the continuous removal of the reaction mixture and the continuous introduction of the OH, SH or NH compound and the ethyne are commenced. The rates are adjusted such that said ratio of quantities of $\geq 0.9$ is ensured in general to be in the range from 0.9 to 0.99. The continuously removed effluent is introduced to a continuous distillative separation step. There, the required O, S or N-alkenyl compound is isolated as a volatile fraction. The liquid product, which contains the basic potassium compound and any unconverted OH, SH or NH compound, as well as higher-boiling byproducts, is partly returned to the reactor. A portion of the liquid product is flushed out to avoid accumulation of byproducts. A quantity of the fresh, basic potassium compound that corresponds to the quantity that has been flushed out is introduced into the reactor.

In a further preferred embodiment, which is particularly preferred for the reaction of the amides, a jet loop reactor is filled with the corresponding O—, S— or N— vinyl compound until it has been filled to the required level, the circulation is switched on and the reactor heated to the required reaction temperature. In this embodiment, the O—, S— or N— vinyl compound that has been introduced can also include a certain proportion of the corresponding OH, SH or NH compound of up to 10%, preferably of up to 5% and particularly preferably of up to 3% by weight. The system is now pressurized with ethyne to the required reaction pressure and the continuous addition of OH, SH or NH compound and the ethyne is commenced. The required quantity of the basic potassium compound is added concurrently. A quantity of the reaction mixture corresponding to the introduced quantities is continuously removed from the reactor and is subjected to a workup step as described above. The basic potassium compound is returned and a corresponding bleed stream is flushed out as described above. The streams introduced into the reactor are adjusted such that a ratio of the quantity of the O, S or N-alkenyl compound to the sum of the quantities of the O, S or N compound and the O, S or N-alkenyl compound of $\geq 0.9$ is ensured.

The continuous process of the invention at a high conversion of the OH, SH or NH compound ensures that the entire synthesis is conducted under the conditions conducted at a consistently high reaction rate. In contrast, prior art industrial batchwise and semicontinuous processes lead to a steady increase in the conversion in the reactor to the required or maximum achievable final conversion and hence plod through a large region of low reaction rate. Even in a continuous process at a conversion smaller than 90%, the reaction would be conducted in a region of low reaction velocity.

The process of the invention allows the simple continuous production of O—, S— and N-alkenyl compounds by reaction of the corresponding O, S or N compound with an acetylene by avoiding the time-, labor- and energy-intensive process steps necessary in the industrially customary batchwise and semicontinuous processes, with higher selectivity, higher space-time yield and therefore higher productivity. The process is carried out under conditions that do not change with time in that the ratios of concentrations in the reactor remain almost the same and the formation of substantially involatile residues is reduced. The quantity of the necessary catalyst (basic alkali or alkaline earth metal compound), and therefore also the costs associated with its production, are appreciably reduced.

The preferred process, which is conducted in the absence of a continuous gas phase in the reaction apparatus, has the further advantage of improved safety, since suitable measures prevent the formation of a reactive gas phase.

EXAMPLES

Example 1 (Comparative Example: Batchwise Process)

A jet loop reactor having an internal volume of about 10.5 l and equipped with a jet nozzle fitted at the head of the reactor and an external circulation pump was charged with about 10.5 kg of a mixture of 5% by weight of potassium cyclohexoxide in cyclohexanol, which was prepared by reaction of cyclohexanol with potassium hydroxide and subsequent distillative removal of the water formed in the reaction. After heating to 159° C., the system was pressurized with ethyne to 2.0 MPa absolute. The reaction mixture was circulated through the jet nozzle by means of a circulation pump and the reacted ethyne was replaced while the total pressure was held constant. Any excess product was removed by a pressure control. The reactor was operated in the absence of a continuous gas phase. After the uptake of ethyne fell to zero, a sample was taken and analyzed by gas chromatography. 91.7% by weight of vinyl cyclohexyl ether and about 0.4% by weight of unconverted cyclohexanol were obtained. The residue was about 6% by weight, consisted predominantly of the potassium cyclohexoxide catalyst and was predominantly undissolved. The remainder is attributable to quantitatively insignificant materials, such as ethyne and ethyl vinyl ether. The conversion of cyclohexanol was 99.6%, based on the cyclohexanol used. The productivity rate was 0.10 kg of vinyl cyclohexyl ether per liter of reaction volume per hour.

Example 2 (Inventive)

The operation of the process that was commenced in example 1 was continued in a continuous fashion with addition of about 0.96 kg/h of a solution of 95% by weight of cyclohexanol and 5% by weight of potassium cyclohexoxide and the necessary quantity of ethyne at 159° C. and a total pressure of 2.0 MPa absolute in the absence of a continuous gas phase. A quantity equivalent to that which was continuously introduced was continuously removed from the reactor, so that the liquid level in the reactor remained approximately constant. A gas chromatographic analysis of the reaction mixture after 4 hours of continuous operation showed that there was 91.8% by weight of vinyl cyclohexyl ether and about 0.4% by weight of unconverted cyclohexanol. Further, it was determined that about 6% by weight of residue was present, which consisted predominantly of the potassium cyclohexoxide catatalyst and was predominantly undissolved. The conversion of cyclohexanol was about 99.5%. The productivity rate was 0.11 kg of vinyl cyclohexyl ether per liter of reaction volume per hour.

Relative to the batchwise process of example 1, the process of the invention in example 2 shows a content of vinyl cyclohexyl ether that is 0.1% by weight higher and a productivity rate that is 10% higher.

Example 3 (Comparative Example: Batchwise Process)

The apparatus of example 1 was charged with about 10.4 kg of a mixture of 4% by weight of potassium imidazolate in imidazole, which was prepared by reaction of imidazole with potassium hydroxide and subsequent distillative removal of the water formed in the reaction. After heating to 175° C., the system was pressurized with ethyne to 2.0 MPa absolute. The reaction mixture was circulated through the jet nozzle by means of a circulation pump and the reacted ethyne was replaced while the total pressure was held constant. Any excess product was removed by a pressure control. After the uptake of ethyne fell to zero, a sample was taken and analyzed by gas chromatography. 81.1% by weight of vinylimidazole was obtained. The residue was about 14% by weight and was partly undissolved. The remainder of imidazole was about 2.0% by weight. The conversion of imidazole was about 97.9%. The productivity rate was 0.10 kg of vinylimidazole per liter of reaction volume per hour.

Example 4 (Inventive)

The operation of the process that was commenced in example 3 was continued in a continuous fashion with the addition, at an increasing rate during the reaction time, of 1.10 kg/h to 1.25 kg/h of a solution of 96% by weight of imidazole and 4% by weight of potassium imidazolate and the necessary quantity of ethyne at 175° C. and a total pressure of 2.0 MPa absolute. A quantity equivalent to the quantity that was continuously introduced was continuously removed from the reactor, so that the liquid level in the reactor remained approximately constant. Gas chromatographic analysis of the reaction mixture after 6 hours of continuous operation showed that 88.9% by weight of vinylimidazole and about 0.5% by weight of unconverted imidazole were present. The residue was about 10% by weight and was partly undissolved. The remainder of imidazole was about 0.5% by weight. The conversion of imidazole was about 99.5%. The productivity rate was therefore 0.16 kg vinylimidazole per liter of reaction volume per hour.

Relative to the discontinuous process of example 3, the process of the invention in example 4 showed a content of vinylimidazole that was 3.8% by weight higher and a productivity rate that was 60% higher.

Example 5 (Comparative Example: Continuous Process at a Conversion <90%)

Similarly to example 3, the reactor was charged with about 10.4 kg of a mixture of 4% by weight potassium imidazolate in imidazole. After heating to 175° C., the system was pressurized with ethyne to 2.0 MPa absolute. The reaction mixture was circulated through the jet nozzle by means of a circulation pump and the reacted ethyne was replaced while the total pressure was held constant. In contrast to example 3, the continuous addition of about 1.10 kg/h of a solution of 96% by weight of imidazole and 4% by weight of potassium imidazolate and the necessary quantity of ethyne was commenced at a composition of the reaction mixture of 72% by weight of vinylimidazole, about 15% by weight of imidazole (corresponds to a conversion of imidazole of about 84.3%) and about 12% by weight of residue, in the present example. The operation of the reactor was continued in a continuous fashion at 175° C. and a total pressure of 2.0 MPa absolute. A quantity corresponding to the continuously introduced quantities was continuously removed from the reactor, so that the liquid level in the reactor remained approximately constant. Analysis of the reaction mixture after 6 hours of continuous operation showed that 65% by weight of vinylimidazole, about 22% by weight of unreacted imidazole and 12% by weight of residue were present. No undissolved components were observed. The conversion of imidazole was about 78%. The productivity rate was therefore about 0.09 kg vinylimidazole per liter of reaction volume per hour.

Example 4, in which the continuous process was commenced at an imidazole conversion of 97.9% and an imidazole content of 81.1% by weight, was carried out by increasing the rate of imidazole/potassium imidazolate to 1.25 kg/h to provide a productivity rate of 0.16 kg vinylimidazole per liter of reaction volume per hour after 6 hours, whereas example 5 provided a productivity rate of 0.09 kg vinylimidazole per liter of reaction volume per hour after 6 hours, even for continuously introduced quantity of imidazole/potassium imidazolate of only 1.10 kg/h. Even an imidazole conversion of 84.3% that was set at the start of the continuous process in example 5 could not be sustained for 6 hours and fell to about 78%.

We claim:

1. A continuous process for the preparation of O—, S— and N-alkenyl compounds by reaction of the corresponding OH, SH or NH compound with an acetylene in the liquid phase in the presence of basic alkali or alkaline earth metal compounds at from 40 to 300° C. and from 0.11 to 5 MPa absolute, which comprises continuously feeding the corresponding OH, SH or NH compound and the acetylene and operating in the absence of a continuous gas phase at a conversion of the corresponding OH, SH or NH compound of $\geq 90\%$.

2. The process as claimed in claim 1, wherein the operating is effected at a conversion of the corresponding OH, SH or NH compound of $\geq 95\%$.

3. The process as claimed in claim 1, wherein the basic alkali or alkaline earth metal compounds are used in an amount of from 0.05 to 15% by weight, based on the reaction mixture.

4. The process as claimed in claim 1, wherein the basic alkali or alkaline earth metal compounds are the sodium or potassium O—, S— or N— compounds that correspond to the OH, SH or NH compounds to be used.

5. The process as claimed in claim 1, wherein
   (a) an amount of a reaction mixture is continuously removed from the reactor that corresponds to the amounts that are continuously fed to the reactor;
   (b) the O—, S— or N-alkenyl compound is separated from the reaction mixture removed from the reactor; and
   (c) the mixture that contains the basic alkali or alkaline earth metal compound is returned to the reactor.

6. The process as claimed in claim 1, wherein the reaction is carried out in a jet loop reactor.

7. The process as claimed in claim 1, wherein O—, S— and N-alkenyl compounds that can be prepared include alkenyl ethers, N-alkenylamides and N-alkenylamines.

8. The process as claimed in claim 1, wherein the acetylene used is ethyne.

9. The process as claimed in claim 1, wherein O—, S— and N-alkenyl compounds that can be prepared include vinyl ethers, N-vinylamides and N-vinylamines.

* * * * *